United States Patent [19]

Dias et al.

[11] Patent Number: 5,308,526
[45] Date of Patent: May 3, 1994

[54] LIQUID PERSONAL CLEANSER WITH MOISTURIZER

[75] Inventors: Luis C. Dias, Cincinnati; Mark L. Kacher, Mason; James R. Schwartz, West Chester, all of Ohio; Ronald S. Baur, Newport, Ky.; David W. Peter; Efrain Torres, both of Cincinnati, Ohio

[73] Assignee: The Procter & Gamble Company, Cincinnati, Ohio

[21] Appl. No.: 909,834

[22] Filed: Jul. 7, 1992

[51] Int. Cl.$^5$ .................. C11D 17/08; C11D 9/24; C11D 9/48
[52] U.S. Cl. .................. 252/125; 252/126; 252/127; 252/130; 252/132; 252/173; 252/174.18; 252/174.23; 252/368; 252/546; 252/DIG. 5; 252/DIG. 14
[58] Field of Search .................. 252/DIG. 5, 14, 13, 252/125, 126, 127, 162, 132, 128, 129, 130, 120, 173, 174.18, 174.23, 367, 368, 546; 424/70, 489, 502; 514/846, 937, 951

[56] References Cited

U.S. PATENT DOCUMENTS

| | | | |
|---|---|---|---|
| 2,438,091 | 3/1948 | Lynch | 260/482 |
| 2,528,378 | 10/1950 | Mannheimer | 260/309.6 |
| 2,658,072 | 11/1953 | Kosmin | 260/513 |
| 3,829,563 | 8/1974 | Barry et al. | 424/70 |
| 4,061,602 | 12/1977 | Oberstar et al. | 252/147 |
| 4,234,464 | 11/1980 | Morshauser | 252/544 |
| 4,310,433 | 1/1982 | Stiros | 252/132 |
| 4,387,040 | 6/1983 | Straw | 252/368 |
| 4,472,297 | 9/1984 | Bolich et al. | 252/531 |
| 4,491,539 | 1/1985 | Hoskins et al. | 252/541 |
| 4,540,507 | 9/1985 | Grollier | 252/174.23 |
| 4,565,647 | 1/1986 | Llenado | 252/354 |
| 4,673,525 | 6/1987 | Small et al. | 252/132 |
| 4,704,224 | 11/1987 | Saud | 252/132 |
| 4,788,006 | 11/1988 | Bolich, Jr. et al. | 252/550 |
| 4,806,262 | 2/1989 | Snyder | 252/90 |
| 4,808,322 | 2/1989 | McLaughlin | 252/121 |
| 4,812,253 | 3/1989 | Small et al. | 252/132 |
| 4,820,447 | 4/1989 | Medcalf, Jr. et al. | 252/117 |
| 4,906,459 | 3/1990 | Cobb et al. | 424/70 |
| 4,923,635 | 5/1990 | Simion et al. | 252/545 |
| 4,941,990 | 7/1990 | McLaughlin | 252/121 |
| 4,954,282 | 9/1990 | Rys et al. | 252/117 |
| 4,976,953 | 12/1990 | Orr et al. | 424/47 |
| 5,002,680 | 3/1991 | Schmidt et al. | 252/90 |
| 5,076,953 | 12/1991 | Jordan et al. | 252/108 |
| 5,132,037 | 7/1992 | Greene et al. | 252/108 |
| 5,147,574 | 9/1992 | MacGilp et al. | 252/108 |
| 5,154,849 | 10/1992 | Visscher et al. | 252/174.15 |
| 5,158,699 | 10/1992 | MacGilp et al. | 252/132 |

OTHER PUBLICATIONS

U.S. Ser. No. 07/909,877 to Kacher et al. filing date Jul. 7, 1992.

Primary Examiner—Paul Lieberman
Assistant Examiner—A. Hertzog
Attorney, Agent, or Firm—Leonard Williamson

[57] ABSTRACT

A very stable mild dispersoidal liquid soap personal cleansing and moisturizing composition comprising:
- (A) from about 5% to about 20% by weight of potassium $C_8$–$C_{22}$ fatty acid soap;
- (B) from about 0.1 to about 7% $C_8$–$C_{22}$ free fatty acid;
- (C) from about 35% to about 70% water; and
- (D) from about 8% to about 35% of a polyol selected from the group consisting of: glycerin, glycerol, propylene glycol, polypropylene glycols, polyethylene glycols, ethyl hexanediol, hexylene glycols, and other aliphatic alcohols; and mixtures thereof;
- (E) from about 0.5% to about 5% petrolatum or emollient having a specific particle size distribution, and
- (F) from about 0.5 to about 5% glycol ester selected from the group consisting of glycol monoesters and diesters of fatty acids with a chainlength from about 10 to about 22, and mixtures thereof.

34 Claims, No Drawings

LIQUID PERSONAL CLEANSER WITH MOISTURIZER

TECHNICAL FIELD

The present invention is related to personal cleansing liquid products, especially personal cleansers and creams for bath or shower which are formulated for mildness, viscosity control, phase stability, and moisturization.

BACKGROUND OF THE INVENTION

Personal cleansing compositions are well known.

The need for mild skin cleansing compositions is made more acute by both the aging of the human population and the ever-increasing environmental insult to which the skin is subject. The mildest skin cleansing products can, at best, produce cleansing without negatively affecting the skin condition. To achieve an improvement in skin condition, the consumer is forced to use a second, separate product often called a "moisturizer". The use of two separate products to achieve the desired skin state is inconvenient and often unpleasant due to the greasy skin feel resultant from many moisturizers. As a result, many persons suffer from the effects of poor skin condition rather than use two separate products.

There is a clear need for a single product which is capable of delivering both mild skin cleansing and a skin conditioning benefit. Many skin cleansing products contain humectant substances which, although effective in topical application, are ineffective in cleansing products. These humectants are ineffective because they are very water soluble and suffer from poor skin substantivity. Hydrophobic emollient materials are generally more substantive to the skin, but are more difficult to incorporate into an aqueous skin cleansing matrix. There are at least two sources of difficulty typically encountered: poor lather effects and physically unstable product.

U.S. Pat. No. 3,829,563, Barry et al., issued Aug. 13, 1974, discloses a liquid skin cleansing composition containing 10-70% by weight petrolatum with more than 95% having a diameter particle size smaller&an 5 micron (claim 1).

U.S. Pat. No. 4,673,525, Small et al., issued Jun. 16, 1987, incorporated herein by reference, discloses mild surfactant based personal cleansing systems, primarily synbars.

Most non-solid soaps comprise mostly "soluble," "unsaturated," or shorter chains, e.g., lauric/oleic soaps for phase stability. This, however, compromises lather quality and/or mildness.

The present invention allows for the incorporation of substantially larger petrolatum particles than the prior art. These larger particles result in greater functional efficacy than previously has been achieved.

OBJECT OF THE INVENTION

One object of this invention is to provide a personal cleansing product which conditions and moisturizes the skin as the product is used. Another object of this invention is to provide a single product which achieves the benefits of using two separate products for cleansing and moisturizing the skin.

A further object is to provide processes for making these products.

It is still another object of the present invention to provide a liquid cleansing bath/shower soap composition which is phase stable, shelf stable, lathers well, and is cosmetically attractive.

It is a further object of the present invention to provide a liquid soap cleansing composition which is relatively mild.

These and other objects of the present invention will become obvious from the detailed description which follows.

SUMMARY OF THE INVENTION

The present invention relates to a stable dispersoidal liquid soap cleansing composition comprising:

(A) from about 5% to about 20% by weight of potassium $C_8$–$C_{22}$ fatty acid soap;
(B) from about 0.1 to about 7% $C_8$–$C_{22}$ free fatty acid;
(C) from about 35% to about 70% water; and
(D) from about 8% to about 35% of a polyol selected from the group consisting of: glycerin (glycerol), propylene glycol, polypropylene glycols, polyethylene glycols, ethyl hexanediol, hexylene glycols, and other aliphatic alcohols; and mixtures thereof;
(E) from about 0.5% to about 5% petrolatum emollient, preferably having a weight average particle size of from 45 microns to about 120 microns; and
(F) from about 0.5 to about 5% glycol ester selected from the group consisting of glycol monoesters and diesters of fatty acids with a chainlength from about 10 to about 22, and mixtures thereof; and wherein said soap plus any surfactant and said free fatty acids plus glycol ester have a preferred ratio of about 1:1 to about 15:1 and more preferably from about 3:1 to about 12:1; and wherein said liquid has a viscosity of from about 500 cps to less than 60,000 cps at 26.7° C. (80°0 F.).

DETAILED DESCRIPTION OF THE INVENTION

This invention relates to a liquid cleansing composition suitable for the cleansing and "conditioning" or "moisturizing" of the skin. The "conditioning" benefit is defined as the deposition of a material on the skin surface which is known to improve skin condition and at a level that surpasses the threshold for a noticeable benefit.

The present invention is concerned with the ability to incorporate petrolatum and/or an equivalent emollient into an aqueous skin cleansing matrix and maintain the larger particle size that results in functional efficacy without producing an unstable product. Formulations and processes have been invented which allow the petrolatum particle size to be improved to have a weight average particle size from about 45 microns to about 120 microns within the product, preferably from about 50-110 microns, more preferably from about 55-110 microns. The larger particles result in improved skin deposition.

The present invention relates to a stable dispersoidal liquid personal soap cleansing composition comprising: 8% to 35% polyol; 0.5% to 5% glycol ester; 35% to 70%, preferably 40% to 65%, water; 5% to 20%, preferably 7% to 19%, of mostly insoluble saturated (low IV) (Iodine Value) higher fatty acid potassium soap; 0.1% to 7%, preferably 0.5 to 5%, of free fatty acids; and 0.5% to 5%, preferably 0.7% or 1% to about 4% or 4.5% petrolatum; and wherein said soap plus any synthetic surfactant and said free fatty acids plus glycol ester have a preferred ratio of about 1:1 to about 15:1 and more preferably from about 3:1 to about 12:1. These ratios ensure stable liquid cleansers containing petrolatum.

A very stable mild dispersoidal liquid soap personal cleansing composition comprising:
(A) from about 5% to about 20% by weight of potassium $C_8$–$C_{22}$ fatty acid soap;
(B) from about 0.1 to about 7% $C_8$–$C_{22}$ free fatty acid;
(C) from about 35% to about 70% water; and
(D) from about 8% to about 35% of a polyol selected from the group consisting of: glycerin (glycerol), propylene glycol, polypropylene glycols, polyethylene glycols, ethyl hexanediol, hexylene glycols, and other aliphatic alcohols; and mixtures thereof;
(E) from about 0.5% to about 5% petrolatum preferably having a weight average particle size of from 45 microns to about 120 microns; and
(F) from about 0.5 to about 5% glycol ester selected from the group consisting of glycol monoesters and diesters of fatty acids with a chainlength from about 10 to about 22, and mixtures thereof; and
wherein said soap plus any synthetic surfactant and said free fatty acids plus glycol ester have a preferred ratio of about 1:1 to about 15:1 and more preferably from about 3:1 to about 12:1; wherein said liquid has a viscosity of from about 500 cps to about 60,000 cps at 26.7° C.; and wherein said fatty acid of said (A) and (B) has an Iodine Value of from zero to about 15. The liquid preferably has a viscosity of less than 60,000 cps at 26.7° C.

When the preferred ratios of soap plus synthetic and free fatty acid plus glycol ester is present, the preferred petrolatum particles are not required to provide an improved liquid cleanser over a comparable liquid cleanser without petrolatum.

However, the preferred improved stable product with an improved moisturizing benefit is achieved with the incorporation of larger sized petrolatum particles into selected fatty acid/soap matrixes. The larger sized petrolatum particles will vary for a liquid, semi-solid, or bar. The key is to select the fatty acid and/or soap matrix as exemplified herein, and mix in the petrolatum using a minimal controlled amount of shear to maintain larger petrolatum particles and achieve a homogeneous stable product, e.g., an improved benefit is also achieved in a semi-solid cleansing cream disclosed in commonly assigned U.S. patent application Ser. No. 909,877 filed of even date, Kacher et al., incorporated herein by reference.

Petrolatum Emollient

A requirement for the present compositions is that they contain from about 0.5% to about 5% petrolatum, preferably having a weight average particle size larger than about 45 microns.

The petrolatum useful in the present invention can be any grade of white or yellow petrolatum recognized in the art as suitable for human application. The preferred type is USP Class III with a melting point (MP) between 122° and 135° F. (50° and 57° C.). Such a material is commercially available as Penreco Snow White Pet USP. The petrolatum of the present invention includes hydrocarbon mixtures formulated with mineral oils in combination with paraffin waxes of various melting points.

Alternatively, the composition of the present invention can contain from about 0.5% to about 15% of a lipophilic emollient selected from the group consisting of: petrolatum; esters of fatty acids; wherein said fatty acids are of structure $$R_1-C(=O)-OR_2$$

and wherein $R_1, R_2 = C_8-C_{22}$, ricinoleate, 12-hydroxy stearic and wherein $R_1$ and/or $R_2$ alkyl chain can be saturated or unsaturated glycerin mono-, di-, and tri-esters; epidermal and sebaceous hydrocarbons such as cholesterol, cholesterol esters, squalene, squalane; silicone oils and gums; mineral oil; lanolin and derivatives and the like; and mixtures thereof.

The petrolatum and/or emollient particle size is alternatively expressed as a particle size distribution with 10% to 80% of the particles being about 5 microns to about 120 microns within the product, preferably 20% to 80% being from about 10–110 or 120 microns, more preferably 25% to 80% from about 30–110 microns, more preferably 60–100 microns.

Method of Making

The liquid cleansing composition is preferably made by the following steps: (1) heating and mixing free fatty acid to provide a stable melt; (2) forming soap in situ by adding aqueous potassium hydroxide to provide a dispersion of soap and free fatty acid; and (3) adding water, polyol and mild, lathering surfactant to said dispersion of Step 2 with mixing; (4) cooling the dispersion of Step 3 to a temperature below the melting point of petrolatum; and (5) adding said petrolatum with mixing and cooling to provide a dispersoidal liquid personal cleansing composition. The soap plus any surfactant and the free fatty acids plus glycol ester have a preferred ratio of about 1:1 to about 15:1 and more preferably from about 3:1 to about 12:1.

Preferably the soap and free fatty acid of Step 1 are heated to a temperature of 75–90 degrees C. Also in Step 4, the cooling rate is rapid to prevent the formation of over large fatty acid and/or glycol ester crystals. Also in Step 3, optionally up to 20% of a mild, lathering synthetic surfactant can be added with minimal shear mixing. The petrolatum in Step 5 is added with controlled minimal shear to provide the dispersoidal liquid personal cleansing composition of this invention.

The Fatty Acid

The fatty acid matter of the present invention has an IV of from zero to about 15, preferably below 10, more preferably below 3.

The compositions contain fatty acids derived from essentially saturated hydrocarbon chainlengths of from about 8 to about 22. These fatty acids may be highly purified individual chainlengths and/or crude mixtures such as those derived from fats and oils. In general, the higher the proposition of longer chainlength fatty acids, the poorer the lather, but the greater the pearlescent appearance and mildness of the product.

The liquid soap cleanser has a viscosity of 500 to less than 60,000 cps, preferably 1,000 cps to about 50,000 cps at about 26.7° C. (80° F.), Brookfield RVTDCP with a Spindle CP-41 at 1 RPM for 3 minutes.

The Soap

The compositions contain soaps derived from essentially saturated hydrocarbon chainlengths of from about 8 to about 22. It is preferred that the soap be the potassium salt, but other soluble soaps can be used. Some sodium, ammonium, triethanolammonium, and/or mixtures thereof, are deemed acceptable, at least in potassium blends. The soaps are preferably prepared in-situ by neutralization of the corresponding fatty acids, but they may also be introduced as preformed soaps.

The liquid soap is called a dispersoid because at least some of the fatty matter at the levels used herein is insoluble. The level of water in the compositions is typically from about 35% to about 70%, preferably from about 40% to about 65%.

Another important attribute of the preferred liquid soap of the present invention is it is phase stable, particularly after storage.

The Polyol

The present invention contains from about 8% to about 35% of a polyol selected from the group consisting of: glycerin (glycerol), propylene glycol, polypropylene glycols, polyethylene glycols, ethyl hexanediol, hexylene glycols, and other aliphatic alcohols; and mixtures thereof; and preferably contains 10-30% of said polyol, preferably the polyol is glycerol.

The term "viscosity" as used herein means both of these viscosities as measured by a Brookfield RVTDCP with a spindle CP-41 at 1 RPM for 3 minutes, unless otherwise specified.

Optionals

If present, the optional components individually generally comprise from about 0.001% to about 10% by weight of the composition, but can be more or less.

Optional thickeners are categorized as cationic, nonionic, or anionic and are selected to provide the desired viscosities. Suitable thickeners are listed in the Glossary and Chapters 3, 4, 12 and 13 of the *Handbook of Water-Soluble Gums and Resins*, Robert L. Davidson, McGraw-Hill Book Co., New York, N.Y., 1980, incorporated by reference herein.

The liquid personal cleansing products can be thickened by using polymeric additives that hydrate, swell or molecularly associate to provide body (e.g., hydroxypropyl guar gum is used as a thickening aid in shampoo compositions).

The nonionic cellulosic thickeners include, but are not limited to, the following polymers:

1. hydroxyethyl cellulose;
2. hydroxymethyl cellulose;
3. hydroxypropyl cellulose; and
4. hydroxybutyl methyl cellulose.

The anionic cellulosic thickener includes carboxymethyl cellulose and the like.

A suitable thickener is hydroxy ethyl cellulose, e.g., Natrosdl ® 250 KR sold by The Aqualon Company.

Another thickener is acrylated steareth-20 methylacrylate copolymer sold as Acrysol ICS-1 by Rohm and Haas Company.

The amount of polymeric thickener found useful in the present compositions is about 0.1% to about 2%, preferably from about 0.2% to about 1.0%.

The liquid soap of the present invention can be made with from about 0.1% or 0.15% to about 5%, preferably from about 0.3% to about 3%, of a cationic polymer selected from the group consisting of: cationic polysaccharides and derivatives, cationic copolymers of saccharides and synthetic monomers, synthetic copolymers and cationic protein derivatives. Detailed lists of suitable cationic polymers are set out in Small et al. and Medcalf et al., U.S. Pat. No. 4,673,525 and U.S. Pat. No. 4,820,447, incorporated herein by reference.

Another component useful in the present invention is a nonionic. The nonionic is polyglycerol ester (PGE).

Groups of substances which are particularly suitable for use as nonionic surfactants are alkoxylated fatty alcohols or alkylphenols, preferably alkoxylated with ethylene oxide or mixtures of ethylene oxide or propylene oxide; polyglycol esters of fatty acids or fatty acid amides; ethylene oxide/propylene oxide block polymers; glycerol esters and polyglycerol esters; sorbitol and sorbitan esters; polyglycol esters of glycerol ethoxylated lanolin derivatives; and alkanolamides and sucrose esters.

The cleansing bath/shower compositions can contain a variety of nonessential optional ingredients suitable for rendering such compositions more desirable. Such conventional optional ingredients are well known to those skilled in the art, e.g., preservatives such as benzyl alcohol, methyl paraben, propyl paraben and imidazolidinyl urea; other thickeners and viscosity modifiers such as $C_8$–$C_{18}$ ethanolamide (e.g., coconut ethanolamide) pH adjusting agents such as citric acid, succinic acid, phosphoric acid, sodium hydroxide, etc.; suspending agents such as magnesium/aluminum silicate; perfumes; dyes; and sequestering agents such as disodium ethylenediamine tetraacetate.

A preferred liquid cleansing composition also contains from about 0.5% to about 10% of an emollient selected from the group consisting of esters of fatty acids; glycerin mono-, di-, and tri-esters; epidermal and sebaceous hydrocarbons such as cholesterol, cholesterol esters, squalene, squalane; lanolin and derivatives, mineral oil, silicone oils and gums, and mixtures thereof and the like.

The Surfactant

An important attribute of the preferred soap personal cleansing product of the present invention is its rich and creamy lather.

The preferred composition also contains from about 0.5% or 1% to about 20%, preferably from about 2 to about 15%, of a high lathering synthetic surfactant.

An important optional component of the present compositions is a lather boosting surfactant. The surfactant, which may be selected from any of a wide variety of anionic (nonsoap), amphoteric, zwitterionic, nonionic and, in certain instances, cationic surfactants, is present at a level of from about 1% to about 10%, preferably from about 2% to about 6% by weight of the product.

The cleansing product patent literature is full of synthetic surfactant disclosures. Some preferred surfactants as well as other cleansing product ingredients are disclosed in the following references:

| Pat. No. | Issue Date | Inventor(s) |
| --- | --- | --- |
| 4,061,602 | 12/1977 | Oberstar et al. |
| 4,234,464 | 11/1980 | Morshauser |
| 4,472,297 | 9/1984 | Bolich et al. |
| 4,491,539 | 1/1985 | Hoskins et al. |
| 4,540,507 | 9/1985 | Grollier |
| 4,565,647 | 1/1986 | Llenado |
| 4,673,525 | 6/1987 | Small et al. |
| 4,704,224 | 11/1987 | Saud |
| 4,788,006 | 11/1988 | Bolich, Jr., et al. |
| 4,812,253 | 3/1989 | Small et al. |
| 4,820,447 | 4/1989 | Medcalf et al. |
| 4,906,459 | 3/1990 | Cobb et al. |

| Pat. No. | Issue Date | Inventor(s) |
|---|---|---|
| 4,923,635 | 5/1990 | Simion et al. |
| 4,954,282 | 9/1990 | Rys et al. |

All of said patents are incorporated herein by reference. A preferred synthetic surfactant is shown the Examples herein. Preferred synthetic surfactant systems are selectively designed for appearance, stability, lather, cleansing and mildness.

It is noted that surfactant mildness can be measured by a skin barrier destruction test which is used to assess the irritancy potential of surfactants. In this test the milder the surfactant, the lesser the skin barrier is destroyed. Skin barrier destruction is measured by the relative amount of radiolabeled water ($^3H$—$H_2O$) which passes from the test solution through the skin epidermis into the physiological buffer contained in the diffusate chamber. This test is described by T. J. Franz in the *J. Invest. Dermatol.*, 1975, 64, pp. 190-195; and in U.S. Pat. No. 4,673,525, Small et al., issued Jun. 16, 1987, incorporated herein by reference, and which disclose a mild alkyl glyceryl ether sulfonate (AGS) surfactant based synbar comprising a "standard" alkyl glyceryl ether sulfonate mixture. Barrier destruction testing is used to select mild surfactants. Some preferred mild synthetic surfactants are disclosed in the above Small et al. patents and Rys et al.

Some examples of good lather-enhancing, mild detergent surfactants are e.g., sodium or potassium lauroyl sarcosinate, alkyl glyceryl ether sulfonate, sulfonated fatty esters, and sulfonated fatty acids.

Numerous examples of other surfactants are disclosed in the patents incorporated herein by reference. They include other alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the surfactants are the alkyl ether sulfates with 1 to 12 ethoxy groups, especially ammonium and sodium lauryl ether sulfates.

Alkyl chains for these surfactants are $C_8$–$C_{22}$, preferably $C_{10}$–$C_{18}$, more preferably $C_{12}$–$C_{14}$. Alkyl glycosides and methyl glucose esters are preferred mild nonionics which may be mixed with other mild anionic or amphoteric surfactants in the compositions of this invention. Alkyl polyglycoside detergents are useful lather enhancers. The alkyl group can vary from about 8 to about 22 and the glycoside units per molecule can vary from about 1.1 to about 5 to provide an appropriate balance between the hydrophilic and hydrophobic portions of the molecule. Combinations of $C_8$–$C_{18}$, preferably $C_{12}$–$C_{16}$, alkyl polyglycosides with average degrees of glycosidation ranging from about 1.1 to about 2.7, preferably from about 1.2 to about 2.5, are preferred.

Anionic nonsoap surfactants can be exemplified by the alkali metal salts of organic sulfuric reaction products having in their molecular structure an alkyl radical containing from 8 to 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

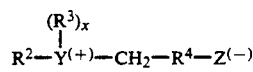

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-P-diethyl-P-3,6,9-tri-oxatetradexocylphosphonio]-2-hydroxypropane-1-phosphate; 3-[N,N-dipropyl-N-3-dodecoxy-2-hydroxypropylammonio]-propane-1-phosphonate; 3-(N,N-dimethyl-N-hexadecylammonio)propane-1-sulfonate; 3-(N,N-dimethyl-N-hexadecylammonio)-2-hydroxypropane-1-sulfonate; 4-[N,N-di(2-hydroxyethyl)-N-(2-hydroxydodecyl)ammonio]-butane-1-carboxylate; 3-[S-ethyl-S-(3-dodecoxy-2-hydroxypropyl)-sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis(2-hydroxyethyl)carboxy methyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine, etc. The sulfobetaines may be represented by coco dimethyl sulfopropyl betaine, stearyl dimethyl sulfopropyl betaine, lauryl bis-(2-hydroxyethyl) sulfopropyl betaine, amido betaines amidosulfobetaines, and the like.

Many cationic surfactants are known to the art. By way of example, the following may be mentioned:
stearyldimethylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride;
laurylpyridinium chloride;
laurylisoquinolium bromide;
ditallow(hydrogenated)dimethyl ammonium chloride;
dilauryldimethyl ammonium chloride; and
stearalkonium chloride.

Many additional nonsoap surfactants are described in McCUTCHEON'S, DETERGENTS AND EMULSIFIERS, 1979 ANNUAL, published by Allured Publishing Corporation, which is incorporated here by reference.

The above-mentioned surfactants can be used in the cleansing bath/shower compositions of the present invention. The anionic surfactants, particularly the alkyl sulfates, the ethoxylated alkyl sulfates and mixtures thereof are preferred. More preferred are $C_{12}$-$C_{14}$ alkyl anionic surfactants selected from the group consisting of sodium alkyl glycerol ether sulfonate, sodium lauroyl sarcosinate, sodium alkyl sulfate, sodium ethoxy (3) alkyl sulfate, and mixtures thereof.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.
2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.
3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).
4. Long chain tertiary amine oxides corresponding to the following general formula:

$$R_1R_2R_3N \rightarrow O$$

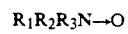

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxy ethyl) amine oxide, dimethyloctylamine oxide, dimethyldecylamine oxide, dimethyltetradecylamine oxide, 3,6,9trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.
5. Long chain tertiary phosphine oxides corresponding to the following general formula:

$$RR'R''P \rightarrow O$$

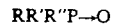

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecyl methyl sulfoxide, 3-hydroxytridecyl methyl sulfoxide, 3-hydroxy-4-dodecoxybutyl methyl sulfoxide.

The pH of the neat cleansing bath/shower compositions herein is generally from about 7.0 to about 9.5, preferably from about 7.5 to about 9 as measured at 25° C.

Assessment of Petrolatum Particle Size

Particle size distribution is measured in neat product under a microscope with a 10× phase contrast objective. The particle size distribution is counted manually. The frequency distribution of the petrolatum particle sizes is converted to a weight distribution by assuming that the petrolatum particles are uniform spheres. The "weight average particle size" is the average particle size based on the arithmetic average of the weight distribution. This standard method for calculating size averages is described in detail in *Handbook of Chemical Microscopy*, Vol. 1, *Third Ed.*, by E. M. Chamot and C. W. Mason (Wiley: New York, 1958).

Quantitation of Petrolatum Deposition

Petrolatum deposition from products is measured by one of two protocols, both modeled after how products are typically used by consumers. One protocol is done "in vitro", while the second is done "in vivo".

In the in vitro protocol, a model skin substrate is used which is a collagen sheet that has a surface topography similar to human skin and has been prehydrated. Small pieces of the substrated are mounted over flask openings to secure them for exposure to lather. The lather is generated in the palms of hands under a controlled procedure (one gram of product plus 3 ml of water for 10 seconds). The mounted substrate is then exposed to the combined lather by overturning the flask and rubbing it on the palm of the hand. This lathering process is continued for 10 seconds and, after allowing the lather to remain on the substrate for 5 seconds, it is rinsed with warm tap water for 10 seconds. The exposed skin substrate is then cut from the mount and dried prior to analysis. The analysis procedure is to submerge the substrate in 1:1 ethanol:heptane and then analysis of this extract by standard gas chromatographic methods.

The in vivo protocol is similar to the in vitro one described above, except the lather generated in the palm of the hand is applied to the opposite forearm. The time that the lather remains on the forearm is 30 seconds (compared to the 5 seconds on the collagen substrate). The deposited petrolatum is then extracted by strapping an open-ended glass cylinder to the forearm and adding the ethanol/heptane solvent to this cylinder. As above, the extract is then analyzed according to standard gas chromatographic methods.

A Method for Making Liquid Cleansing Moisturizers

A method of manufacture of the product of the present invention can use standard industry equipment. Specifically, a general process for a 6000 gram size batch using a 4.5 gallon jacketed tank agitated by a Lightning Mixer (Model TS2010) fitted with a three prong propeller size agitator with blades measuring one inch. However, mixing times will vary with equipment, batch size, etc.

1. The fatty acids (the oil phase), antimicrobial (if added), etc. is added to a sanitary agitated and jacketed stainless steel vessel;
2. The oil phase is heated to about 80° C.
3. Polyol liquids (e.g., propylene glycol) and some surfactant are added to the heated oil phase.
4. In a separate container, a water phase is prepared containing polymers, polyol liquids (e.g., glycerin), and water, and heated to 80° C. with agitation.
5. The appropriate base (e.g., potassium hydroxide) for an in situ soap formation is added and mixed into the oil phase.
6. Next, the water phase is added and mixed to the oil phase/soap vessel.
7. Glycol ester is melted and mixed into (6) at about 80° C.
8. Any additional surfactant is added to (7) at about 80° C.
9. The product of (8) is cooled to about 45° C. at which time other minors such as preservatives and perfumes can be added.
10. Petrolatum emollient is added and mixed to (9) at a temperature of between about 35° C. to about 45° C. or about or at a temperature below its melting point.

Alternatively, the product of Step 9 may stand prior to adding materials such as petrolatum. In case of the product standing, the product of Step 9 is reheated to about 35° C., before the petrolatum is added.

In the method of making the product of this invention, the large petrolatum particle size is controlled by mix time and addition temperature. The shorter the mix time and the lower the temperature, the higher the proportion of larger petrolatum emollient particles is achieved.

To recap, some preferred liquid product comprises: (1) from about 5% to about 20% soaps of fatty acids with hydrocarbon chainlengths of from about 8 to about 22, preferably from about 7% to about 19% essentially saturated potassium salts; (2) from 0.1% to about 7% free fatty acid derived from hydrocarbon chainlengths of from about 8 to about 22, preferably from about 0.5% to about 5% essentially saturated fatty acids; (3) from about 8% to about 35% polyol liquids, preferably from about 10% to about 30% glycerin, propylene glycol and mixtures thereof; (4) from about 0.5% to about 5% petrolatum preferably of weight average particle size larger than about 45 microns; (5) from 0% to about 20% lathering, mild co-surfactants, preferably from about 2% to about 15% of said surfactant; (6) from about 35% to about 70% water, preferably from about 40% to about 65% water; (7) optionally present are certain cationic polymers at a level from 0% to about 5%, preferably from about 0.05% to about 3%; (8) from about 0.5% to about 5% glycol esters, preferably from about 1.0% to about 4% glycol diesters in which the hydrocarbon chainlengths are from about 14 to about 20; (9) a preferred ratio of soap plus surfactant system to free fatty acid and glycol esters of from about 1:1 to about 15:1, more preferably from about 3:1 to about 12:1.

EXAMPLES AND FORMULAS

The following examples and formulas are illustrative and are not intended to limit the scope of the invention(s). The preferred method of making the liquid cleansing compositions of the present invention is set out above. All levels, ranges, temperatures, results, etc., used herein are approximations, unless otherwise specified. All formula percentages are expressed as a weight percentage unless otherwise specified.

EXAMPLES 1-4

Examples 1-4 (Table 4) are liquid compositions that show several of products of the present invention to demonstrate varying levels of petrolatum and/or equivalent and varying levels of soap plus any surfactant and free fatty acids plus glycol ester. Example 3 is a highly preferred liquid cleansing product of the present invention.

| Ingredients: | Examples | | | |
|---|---|---|---|---|
|  | 1 | 2 | 3 | 4 |
| Water | 50.2 | 49.0 | 40.6 | 49.0 |
| Stearic Acid | — | 0.22 | 0.67 | 0.22 |
| Palmitic Acid | — | 0.38 | 1.13 | 0.38 |
| Myristic Acid | 0.9 | 0.45 | 1.35 | 0.45 |
| Lauric Acid | 0.9 | 0.45 | 1.35 | 0.45 |
| In situ potassium soap | 20.0 | 17.0 | 11.0 | 17.0 |
| Glycerin | 9.0 | 15.0 | 15.0 | 15.0 |
| Propylene Glycol | — | 7.0 | 10.0 | 7.0 |
| Na$_5$Pentetate | 0.02 | 0.02 | 0.02 | 0.02 |
| Na$_4$Etidronate | 0.02 | 0.02 | 0.02 | 0.02 |
| Di Stearyl Di Methyl Ammonium Chloride | 0.3 | — | — | — |
| Sodium Lauroyl Sarcosinate | 8.0 | 6.0 | 6.0 | 6.0 |
| Hydroxy Ethyl Cellulose | 0.2 | — | — | — |
| Polyethylene Glycol 600 | 4.0 | — | — | — |
| Sodium Laureth Sulfate | — | — | 2.0 | — |
| Coco Amido Propyl Betaine | — | — | 4.0 | — |
| Cetyl Ricinoleate | — | — | — | 0.75 |
| Polyquaternium-10 | 0.3 | 0.6 | 1.0 | 0.6 |
| Fragrance | 0.7 | 0.6 | 0.6 | 0.6 |
| Ethyleneglycol Distearate | 2.0 | 1.0 | 1.5 | 1.0 |
| Preservatives | 0.8 | 0.8 | 0.8 | 0.8 |
| Petrolatum | 2.7 | 1.5 | 3.0 | 0.75 |

The stable liquid cleansers of Examples 1-4 are prepared in accordance with the method set out above. Care is taken to add the petrolatum in Step 10 at a temperature below the MP of the petrolatum, using gentle mixing to ensure large petrolatum particles, preferably having weight average sizes over 45 micron.

The soap/synthetic surfactant//fatty acid/glycol ester ratios for Examples 1-4 are respectively about: 7.4:1, 9.2:1, 3.8:1, and 9.2:1.

These ratios provide stable liquids comprising the petrolatum. Examples 1-4 are all milder than comparable liquid cleansing compositions without petrolatum, as well as liquids with smaller petrolatum particles. It is noted that Example 4 is a milder liquid cleanser than Example 2, and Example 3 is milder than Example 4. Thus, Example 3 is highly preferred.

What is claimed is:

1. A stable dispersoidal liquid soap cleansing and moisturizing composition, by weight, comprising:

(A) from about 5% to about 20% by weight of potassium $C_8$-$C_{22}$ fatty acid soap;
    (B) from about 0.1 to about 7% $C_8$-$C_{22}$ free fatty acid;
    (C) from about 35% to about 70% water; and
    (D) from about 8% to about 35% of a polyol selected from the group consisting of: glycerin (glycerol), propylene glycol, polypropylene glycols, polyethylene glycols, ethyl hexanediol, hexylene glycols; and mixtures thereof;
    (E) from about 0.5% to about 5% petrolatum wherein 20% to 80% of the petrolatum particles have a particle size of from about 10 microns to about 120 microns;
    (F) from about 0.5 to about 5% glycol ester selected from the group consisting of glycol monoesters and diesters of fatty acids with a chain length from about 10 to about 22, and mixtures thereof; and
    (G) from 0% to 20% of a synthetic surfactant; and
    wherein said liquid composition has a viscosity of from about 500 cps to less than 60,000 cps at 27.6° C. (80° F.).

2. A liquid cleansing composition of claim 1 wherein said fatty acid of said (A) and (B) has an Iodine Value of from zero to about 15; and wherein said soap (plus any synthetic surfactant) and said free fatty acid plus said glycol ester have a ratio of from about 1:1 to about 15:1.

3. A liquid cleansing composition of claim 2 wherein said composition contains from about 0.7% to about 4% of said petrolatum with a weight average particle size of from 50 microns to 110 microns; and wherein said Iodine Value is less than 10 and wherein said liquid composition has a viscosity of 1,000 cps to about 50,000 cps and wherein said ratio is about 3:1 to about 12:1.

4. A liquid cleansing composition of claim 2 wherein said composition contains petrolatum at a level of about 1% to about 4% and has a MP of from about 50° C. to about 60° C.; and wherein said fatty acid Iodine Value is less than 3.

5. A liquid cleansing composition according to claim 1 comprising from about 1% to about 20% of a high lathering synthetic surfactant.

6. A liquid cleansing composition according to claim 1 wherein the ratio of potassium soap (plus any synthetic surfactant) to free fatty acid plus glycol ester is from about 3:1 to about 12:1; and wherein said soap and free fatty acid is highly saturated and has an Iodine Value of from zero to about 10; and wherein said fatty acid is composed of alkyl chain lengths ranging from $C_8$ to $C_{20}$; and wherein said composition contains from about 2% to about 15% of a higher lathering synthetic surfactant.

7. A liquid cleansing composition according to claim 1 wherein said composition contains from about 10% to about 30% glycerol.

8. A liquid cleansing composition according to claim 6 wherein said soap and free fatty acid has an Iodine Value of from zero to 3 and wherein said synthetic surfactant is lauroyl sarcosinate with cations selected from the group consisting of sodium or potassium, mixtures thereof.

9. A liquid cleansing composition according to claim 8 wherein said composition contains from about 0.15 to about 5% cationic polymer selected from the group consisting of:

(I) cationic polysaccharides
    (II) cationic copolymers having monomers selected from saccharides and synthetic monomers (III) synthetic polymers selected from the group consisting of:
(A) cationic polyalkylene imines,
(B) cationic ethoxypolyalkylene imines, and
(C) cationic poly(N-(3-(dimethylammonio)-propyl(N'-(3-ethyleneoxyethylene dimethylammonio)propyl)urea dichloride); and
(IV) cationic protein derivatives.

10. A liquid cleansing composition according to claim 9 wherein the cationic polymer level is from about 0.3% to about 3%.

11. A liquid cleansing composition according to claim 1 wherein said composition also contains from about 0.5% to about 10% of an emollient selected from the group consisting of esters of fatty acids; glycerin mono-, di-, and tri-esters; epidermal and sebaceous hydrocarbons cholesterol, cholesterol esters, squalene, squalane; lanolin and derivatives; mineral oil, silicone oils and gums, and mixtures thereof.

12. A stable liquid cleansing composition according to claim 1 wherein said composition is made by the following steps:
1. heating and mixing said free fatty acid to provide a stable melt;
2. forming a heated aqueous potassium dispersion of soap and said free fatty acid;
3. adding balance of said water, polyol (D), and optionally up to 20% of a mild, lathering synthetic surfactant to said dispersion (minimal shear) (2), with mixing;
4. cooling the dispersion of Step 3 to a temperature below the melting point of said petrolatum (E);
5. adding said petrolatum with controlled minimal shear mixing to provide said dispersoidal liquid personal cleansing composition.

13. A liquid cleansing composition according to claim 12 comprising potassium soap made in situ with potassium hydroxide.

14. The stable liquid cleansing composition of claim 12 wherein said soap and said free fatty acid of Step 1 are heated to a temperature of from about 75° C. to about 90° C.

15. The liquid cleansing composition of claim 12 wherein said cooling is conducted at a rapid rate to prevent the formation of over large fatty acid and glycol ester crystals.

16. A stable dispersoidal liquid soap cleansing and moisturizing composition, by weight, comprising:
(A) from about 5% to about 20% by weight of potassium $C_8$-$C_{22}$ fatty acid soap;
(B) from about 0.1 to about 7% $C_8$-$C_{22}$ free fatty acid;
(C) from about 35% to about 70% water; and
(D) from about 8% to about 35% of a polyol selected from the group consisting of: glycerin (glycerol), propylene glycol, polypropylene glycols, polyethylene glycols, ethyl hexanediol, hexylene glycols; and mixtures thereof;
(E) from about 0.5 to about 5% glycol ester selected from the group consisting of glycol monoesters and diesters of fatty acids with a chain length from about 10 to about 22, and mixtures thereof;
(F) from about 0.5% to about 5% of a lipophilic emollient wherein said emollient is selected from the group consisting of: petrolatum, esters of fatty acids, glycerin mono-, di-, and tri-esters; epidermal and sebaceous hydrocarbons, silicone oils and gums, lanolin and derivatives, and mixtures thereof wherein 20% to 80% of the emollient particles have a particle size of from about 10 to about 120 microns; and
wherein said liquid composition has a viscosity of from about 500 cps to less than 60,000 cps at 27.6° C. (80° F.).

17. The composition of claim 16 wherein said emollient is selected from the group consisting of petrolatum and esters of fatty acids wherein said fatty acids are of structure

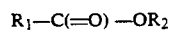

and wherein
$R_1, R_2 = C_8$-$C_{22}$, ricinoleate, 12-hydroxy stearic and wherein $R_1$ and/or $R_2$ alkyl chain can be saturated or unsaturated.

18. The composition of claim 17 wherein said emollient is petrolatum.

19. The composition of claim 16 wherein from about 25% to about 80% of said emollient particles have a particle size of from about 30 micron to about 110 micron.

20. The composition of claim 19 wherein from about 25% to about 80% of said emollient particles have a particle size of from about 60 micron to about 100 micron.

21. A stable dispersoidal liquid soap cleansing and moisturizing composition, by weight, comprising:
(A) from about 5% to about 20% by weight of potassium $C_8$-$C_{22}$ fatty acid soap;
(B) from about 0.1 to about 7% $C_8$-$C_{22}$ free fatty acid;
(C) from about 35% to about 70% water; and
(D) from about 8% to about 35% of a polyol selected from the group consisting of: glycerin (glycerol), propylene glycol, polypropylene glycols, polyethylene glycols, ethyl hexanediol, hexylene glycols; and mixtures thereof;
(E) from about 0.5% to about 5% petrolatum wherein 20% to 80% of the petrolatum particles have a particle size of from about 10 to about 120 microns; and
(F) from about 0.5 to about 5% gylcol ester selected from the group consisting of glycol monoesters and diesters of fatty acids with a chain length from about 10 to about 22 , and mixtures thereof;
wherein said fatty acid of said (A) and (B) has an Iodine Value of from zero to about 15; wherein said soap (plus any synthetic surfactant) and said free fatty acid plus said glycol ester have a ratio of from about 1:1 to about 15:1 and
wherein said liquid composition has a viscosity of from about 500 cps to less than 60,000 cps at 27.6° C. (80° F.).

22. A liquid cleansing composition of claim 21 wherein said composition contains from about 0.7% to about 4% of said petrolatum; and wherein said Iodine Value is less than 10 and wherein said liquid composition has a viscosity of 1,000 cps to about 50,000 cps and wherein said ratio is about 3:1 to about 12:1.

23. A liquid cleansing composition of claim 21 wherein said composition contains petrolatum at a level of about 1% to about 4% and has a MP of from about 50° C. to about 60° C.; and wherein said fatty acid Iodine Value is less than 3.

24. A liquid cleansing composition according to claim 21 comprising from about 1% to about 20% of a high lathering synthetic surfactant.

25. A liquid cleansing composition according to claim 21 wherein the ratio of potassium soap (plus any synthetic surfactant) to free fatty acid plus glycol ester is from about 3:1 to about 12:1; and wherein said soap and free fatty acid is highly saturated and has an Iodine Value of from zero to about 10; and wherein said fatty acid is composed of alkyl chain lengths ranging from $C_8$ to $C_{20}$; and wherein said composition contains from about 2% to about 15% of a higher lathering synthetic surfactant.

26. A liquid cleansing composition according to claim 21 wherein said composition contains from about 10% to about 30% glycerol.

27. A liquid cleansing composition according to claim 25 wherein said soap and free fatty acid has an Iodine Value of from zero to 3 and wherein said synthetic surfactant is lauroyl sarcosinate with cations selected from the group consisting of sodium or potassium, and mixtures thereof.

28. A liquid cleansing composition according to claim 27 wherein said composition contains from about 0.15 to about 5% cationic polymer selected from the group consisting of:
(I) cationic polysaccharides
(II) cationic copolymers having monomers selected from saccharides and synthetic monomers,
(III) synthetic polymers selected from the group consisting of:
   (A) cationic polyalkylene imines,
   (B) cationic ethoxypolyalkylene imines, and
   (C) cationic poly(N-(3-(dimethylammonio)-propyl(N'-(3-ethyleneoxyethylene dimethylammonio)propyl)urea dichloride); and
(IV) cationic protein derivatives.

29. A liquid cleansing composition according to claim 28 wherein the cationic polymer level is from about 0.3% to about 3%.

30. A liquid cleansing composition according to claim 21 wherein said composition also contains from about 0.5% to about 10% of an emollient selected from the group consisting of esters of fatty acids; glycerin mono-, di-, and tri-esters; epidermal and sebaceous hydrocarbons cholesterol, cholesterol esters, squalene, squalane; lanolin and derivatives; mineral oil, silicone oils and gums, and mixtures thereof.

31. A stable liquid cleansing composition according to claim 21 wherein said composition is made by the following steps:
1. heating and mixing said free fatty acid to provide a stable melt;
2. forming a heated aqueous potassium dispersion of soap and said free fatty acid;
3. adding balance of said water, polyol (D), and optionally up to 20% of a mild, lathering synthetic surfactant to said dispersion (minimal shear) (2), with mixing;
4. cooling the dispersion of Step 3 to a temperature below the melting point of said petrolatum (E);
5. adding said petrolatum with controlled minimal shear mixing to provide said dispersoidal liquid personal cleansing composition.

32. A liquid cleansing composition according to claim 31 comprising potassium soap made in situ with potassium hydroxide.

33. The stable liquid cleansing composition of claim 31 wherein said soap and said free fatty acid of Step 1 are heated to a temperature of from about 75° C. to about 90° C.

34. The liquid cleansing composition of claim 31 wherein said cooling is conducted at a rapid rate to prevent the formation of over large fatty acid and glycol ester crystals.

* * * * *